United States Patent

Busch, Jr. et al.

[11] Patent Number: 5,811,084
[45] Date of Patent: Sep. 22, 1998

[54] LONG WEARING FINGER NAIL ENAMELS CONTAINING FLUORIDE COMPOUNDS

[75] Inventors: Francis W. Busch, Jr., Southbury; Kimberly Ann Therrien, Plantsville, both of Conn.

[73] Assignee: Pro Strong Inc., Oakville, Conn.

[21] Appl. No.: 864,337

[22] Filed: May 28, 1997

[51] Int. Cl.$^6$ .............................. A61K 6/00; A61K 7/00; A61K 7/04

[52] U.S. Cl. ............................................. 424/61; 424/401

[58] Field of Search ............................... 424/61, 673, 401

[56] References Cited

U.S. PATENT DOCUMENTS

| | | | |
|---|---|---|---|
| 4,919,920 | 4/1990 | Devos | 424/61 |
| 5,275,807 | 1/1994 | Pappas et al. | 424/61 |

*Primary Examiner*—Thurman K. Page
*Assistant Examiner*—Sharon Howard

[57] ABSTRACT

Metallic fluoride salts characterized by a water solubility of 0.05 to 2.00 grams of fluoride per 100 grams of water and an organic solvent solubility of less than 0.10 grams of solid per 100 grams of solvent are added to colored or clear finger nail enamel compositions to provide nail enamels which are unaltered in color rendition, exhibit excellent adhesion to finger nails and, when applied to finger nails, exhibit substantially increased duration of wear.

6 Claims, No Drawings

LONG WEARING FINGER NAIL ENAMELS CONTAINING FLUORIDE COMPOUNDS

BACKGROUND OF THE INVENTION

U.S. Pat. No. 5,478,551 discloses a non-aqueous organic composition for hardening and strengthening fingernails and toenails of human beings comprising a cosmetically acceptable organic vehicle containing a nail strengthening agent in the form of ammonium hexafluorophosphate dissolvable in said vehicle and providing an effective amount of fluoride.

U.S. Pat. No. 4,919,920 discloses an aqueous inorganic composition for use in strengthening and hardening finger nails and toe nails which takes the form of an aqueous vehicle having dissolved therein an aqueous keratin hardening and strengthening agent containing an effective amount of fluoride ion, the composition having a pH of 3.8 to 8.

In view of such known uses of flouride compounds in strengthening and hardening nails, applicant concluded that it might be advantageous to incorporate flouride compounds into otherwise known finger nail enamels.

In experimenting with otherwise known colored nail enamel compositions, applicant discovered that the addition of ammonium hexafluorophosphate to such compositions caused chemical reactions with the color components which totally distorted the color of the composition and rendered it unusable as a nail polish.

However, applicant, in conducting additional experiments, made the surprising discovery that the addition of certain metallic flouride salts in otherwise known colored or clear nail enamel compositions not only produced nail enamel unaltered in color rendition with excellent adhesion to finger nails but also when applied to finger nails exhibited substantially increased duration of wear. These metallic flouride salts, in contradiction to the teachings of the two patents cited above, have very limited solubility in water and are virtually insoluble in the organic solvents used in the manufacture of nail enamel.

SUMMARY OF THE INVENTION

In accordance with the principles of this invention, metallic fluoride salts having very limited solubility in water and essentially insoluble in the organic solvents are added to colored or clear finger nail enamel compositions to provide nail enamels which are unaltered in color rendition, exhibit excellent adhesion to finger nails and, when applied to finger nails, exhibits substantially increased duration of wear.

The water solubility of the flouride compounds employed in this invention range from 0.05 grams per 100 grams of water to 2.00 grams per 100 grams of water. These fluoride compounds are essentially insoluble in organic solvents, exhibiting a solubility of less than 0.10 grams of solid per 100 grams of solvent.

The metallic fluoride salts employed herein are lithium flouride [solubility 0.13 grams per hundred grams of water]; anhydrous zinc fluoride [solubility 0.052 grams per hundred grams of water]; zinc fluoride tetra hydrate [solubility 1.516 grams per hundred grams of water]; and zirconium tetra fluoride [solubility 1.32 grams per hundred grams of water].

The amounts of fluoride compounds utilized in this invention range upward from a minimum of about 0.1% by weight of enamel. The maximum percentage addition can substantially exceed 0.4% but present experience indicates that additions beyond 2.0% do not appear to increase the beneficial effect.

Finger nail enamels, in accordance with the invention, in addition to the metallic fluoride salts, contain only known components typically used in known percentages to manufacture nail enamels. These known components in known percentages are well known in the art, as disclosed for example in U.S. Pat. No. 3,864,294 and are only identified herein generically except for the specific components set forth in the examples given below. Since the percentages used are unchanged except for the extremely small additions of the fluoride salts, such percentages are not given herein except in the examples given below. These additional components include a primary film forming ingredient; a supplemental film forming resin; plasticizers; organic solvents for the resins, film formers and plasticizers; and when color pigments are added, these color producing pigments are known to the art as metal flakes of organic dyes.

Known pearlescent pigments can be used in substitution of or in combination with these pigments.

A known pigment suspending agent such as stearlakonium hecktorite can be added during manufacture to stabilize the pigment dispersion in the enamel.

The methods for manufacturing the enamels are well known as disclosed in the above identified U.S. Pat. No. 3,864,294 and are unchanged except for the addition of the metal fluoride salts.

Specific examples of nail enamel compositions in accordance with the invention are set forth below.

| EXAMPLES | 1 | 2 | 3 | 4 | 5 | 6 |
|---|---|---|---|---|---|---|
| NITROCELLULOSE ½ SECOND R.S. GRADE | 20.00 | 16.00 | 19.00 | 16.00 | 16.00 | 16.00 |
| TOSLAMIDE EPOXY RESIN | 9.0 | 9.0 | 9.0 | 9.0 | 9.0 | 9.0 |
| ETHYL ACETATE | 20.0 | 16.0 | 16.0 | 16.0 | 16.0 | 16.0 |
| BUTYL ACETATE | 36.0 | 33.0 | 33.0 | 33.0 | 33.0 | 33.0 |
| DIBUTYL PHTHLATE | 7.5 | 7.5 | 7.5 | 7.5 | 7.5 | 7.5 |
| ISOPROPYL ALCOHOL | 2.0 | 2.0 | 2.0 | 2.0 | 2.0 | 2.0 |
| ANHYDROUS ETHYL ALCOHOL | 5.0 | 5.0 | 5.0 | 5.0 | 5.0 | 5.0 |
| CAMPHOR | 3.5 | 3.5 | 3.5 | 3.5 | 3.5 | 3.5 |
| ETOCRYLENE | 0.5 | 0.5 | 0.5 | 0.5 | 0.5 | 0.5 |
| LITHIUM FLOURIDE | 0.1–2.0 | 2.0 | 2.0 | | | |
| ANHYDROUS ZINC FLOURIDE | | | | 2.0 | | |
| ZINC FLOURIDE TETRA HYDRATE | | | | | 2.0 | |
| ZIRCONIUM TETRA FLOURIDE | | | | | | 2.0 |
| COLOR PIGMENTS | | 10.0 | 5.0 | 10.0 | 10.0 | 10.0 |
| PEARLESCENT PIGMENTS | | | 2.0 | | | |
| STEARALKONIUM HECTORITE OR BENTONITE | | 10 | 1.0 | 1.0 | 1.0 | 1.0 |

TEST RESULTS

The formula of example 1, without the lithium flouride addition, is a known clear enamel. This known enamel was tested against the formula of example 1 with the flouride addition by wearing same on alternate fingers of women who agreed to become panelists. It was decided that an enamel exhibited satisfactory wear if 90% of the enamel remained on the nail at the end of a one week tests period.

100% of the panelists reported that the flouride containing enamel exhibited satisfactory wear while only 1 0% of the panelists rated the non-flouride enamel as satisfactory.

The same test was repeated comparing the formula of example 2 containing flouride with the identical formula without flouride. 90% of the panelists reported that the flouride containing enamel exhibited satisfactory wear while only 10% of the panelists rated the non-flouride enamel as satisfactory.

Similar tests of other formulas confirmed these test results.

While the invention has been disclosed with particular emphasis on detailed examples and test results, the protection solicited is to be limited only by the terms of the claims which follow.

What is claimed is:

1. A finger nail enamel which when applied to finger nails exhibits substantially increased duration of wear and comprises:

a primary film forming ingredient;

supplemental film forming resins;

plasticizers;

organic solvents for the resins, film formers and plasticizers; and at least one metallic flouride salt characterized by a water solubility of 0.05 to 2.00 grams of flouride per 100 grams of water and an organic solvent solubility of less than 0.10 grams of solid per 100 grams of solvent, the enamel containing between 0.01% and 2.0% by weight of metallic flouride salt.

2. The enamel of claim 1 wherein the metallic flouride salt is selected from the group consisting of lithium flouride; anhydrous zinc fluoride; zinc fluoride tetrahydrate; and zirconium tetrafluoride.

3. The enamel of claim 1 further including color pigments in the form of metallic lakes of organic dyes.

4. The enamel of claim 3 further including or comprising a color pigment suspending agent.

5. A method of increasing the duration of wear of nail enamel applied to finger nails of a wearer which comprises the steps of:

preparing a nail enamel composed of a primary film forming ingredient; supplemental film forming resins; plasticizers; organic solvents for the resins, film formers and plasticizers; and at least one metallic flouride salt chacterized by a water solubility of 0.5 to 2.00 grams of fluoride per 100 grams of water and an organic solvent solubility of less than 0.10 grams of solid per 100 grams of solvent, the enamel containing between 0.01% and 2.0% by weight of metallic flouride salt;

applying said enamel to said finger nails; and allowing said enamel to remain on said nails for a period of one week.

6. The method of claim 5 wherein said enamel also contains color pigments in the form of metallic lakes of organic dyes.

\* \* \* \* \*